United States Patent [19]

Nguyen et al.

[11] Patent Number: 5,650,137
[45] Date of Patent: Jul. 22, 1997

[54] COSMETIC COMPOSITION CONTAINING A SUPEROXIDE DISMUTASE AND A PORPHYRIN

[75] Inventors: Quang Lan Nguyen, Antony; Christian Colin, Paris, both of France

[73] Assignee: L'Oreal, Paris, France

[21] Appl. No.: 407,677

[22] Filed: Mar. 21, 1995

[30] Foreign Application Priority Data

Mar. 21, 1994 [FR] France .................. 94 03271

[51] Int. Cl.$^6$ .................. A61K 7/40; A61K 7/00
[52] U.S. Cl. .................. 424/59; 424/401; 424/70.9; 424/195.1
[58] Field of Search .................. 424/401, 195.1, 424/70.1, 70.9, 59

[56] References Cited

U.S. PATENT DOCUMENTS

| | | | |
|---|---|---|---|
| 4,129,644 | 12/1978 | Kalopissis et al. | 424/59 |
| 4,957,740 | 9/1990 | Wilder | 424/94.4 |
| 5,352,438 | 10/1994 | N'Guyen | 424/45 |

FOREIGN PATENT DOCUMENTS

| | | |
|---|---|---|
| 0 504 040 | 9/1992 | European Pat. Off. . |
| 2 287 899 | 5/1976 | France . |
| 2 675 997 | 11/1992 | France . |
| 92 19224 | 11/1992 | WIPO . |
| 94 02484 | 2/1994 | WIPO . |

*Primary Examiner*—Sallie M. Gardner
*Attorney, Agent, or Firm*—Oblon, Spivak, McClelland, Maier & Neustadt, P.C.

[57] ABSTRACT

The invention relates to a cosmetic and/or dermatological composition comprising at least one superoxide dismutase and at least one porphyrin. In a composition of this kind the porphyrin synergically reinforces the anti-free radical action of the superoxide dismutase.

The composition is used in particular to combat cell ageing and/or for the protection of the skin, hair and/or mucosae against the harmful and/or unaesthetic effects caused by oxygen-containing free radicals.

11 Claims, No Drawings

COSMETIC COMPOSITION CONTAINING A SUPEROXIDE DISMUTASE AND A PORPHYRIN

BACKGROUND OF THE INVENTION

1. Field of the Invention

The present invention relates to cosmetic and/or dermatological compositions which contain a superoxide dismutase (SOD) together with a porphyrin.

2. Discussion of the Background

Such compositions, which are used topically, make it possible to combat skin ageing and/or to protect the skin against the effects of free radicals which are induced, for example, by atmospheric pollutants and/or by ultraviolet radiation. It fact known that the toxicity of atmospheric pollutants, especially gaseous pollutants such as sulphur dioxide, ozone and oxides of nitrogen, is linked to their activity as initiators of free radicals, which are the source of oxidation phenomena which cause damage to the cells of living beings. The cells of organs which are in direct and permanent contact with the external environment, such as the skin, scalp and some mucosae, are particularly sensitive to these effects of the gaseous pollutants, which are manifested in particular in accelerated ageing of the skin, with a dull complexion and the premature formation of wrinkles and lines, and also in a reduction in the vigor and a dull appearance of the hair.

It is known that superoxide dismutases are enzymes which are capable of inducing the dismutation of superoxide ions in accordance with the reaction:

$$2O^-_2 + 2H^+ \rightarrow H_2O_2 + O_2$$

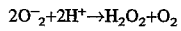

Numerous superoxide dismutases are known. For example, a superoxide dismutases extracted from bovine erythrocytes (Markovitz, *J. Biol. Chem.* 234, p. 40, 1959) and superoxide dismutases extracted from *Escherichia coli* (Keele and Fridovich, *J. Biol. Chem.*, 245, p. 6176, 1970) are known. U.S. Pat. No. 3,920,521 describes superoxide dismutases extracted from marine bacterial strains, and also processes for their preparation.

Superoxide dismutases make it possible to protect the skin and hair, especially while maintaining the integrity of the natural keratinous structure, as described for example by U.S. Pat. No. 4,129,644. In addition, superoxide dismutases improve the skin cell respiration and maintain or enhance the qualities of the skin such as softness to the touch, suppleness and elasticity. Their presence in compositions for hair also enables the condition of the scalp to be maintained or enhanced while also protecting the skin on the hands of the person applying these compositions.

The superoxide dismutases additionally protect the skin against the inflammatory phenomena caused by ultraviolet radiation and against the accelerated ageing of the skin, especially under the influence of such radiation.

By virtue of these various properties, superoxide dismutases can be used in cosmetic compositions for the skin, hair and/or mucosae and in pharmaceutical compositions for dermatological use.

Superoxide dismutases act against oxygen-containing free radicals. The superoxide ion $O^-_2$ (active oxygen) is a radical ion whose instability and reactivity make it toxic because it gives rise to highly damaging hydroxyl free radicals (.OH), especially in the presence of metal ions. Superoxide dismutases exert a protective effect, in particular, by trapping the superoxide ions, and therefore constitute a biological defense system against the harmful effects of the oxygen-containing free radicals.

Unfortunately, superoxide dismutases used alone in a cosmetic composition have a degree of effectiveness which is insufficient to trap completely the oxygen-containing free radicals. In order to solve this problem, it has already been envisaged to combine it with a sequestering agent of the phosphonic type (see U.S. Pat. No. 5,352,438).

The use of hemin and hematin to protect the skin from sunlight and to prevent the ageing of the skin is known (JP-A-02019311). FR-A-2,693,904 discloses the use of chlorophylls for restructuring the skin and, in addition, for preventing the ageing of the skin. However, these documents in no way describe nor suggest to use a porphyrin with a superoxide dismutase with the intention of reinforcing, with synergy, the activity of the latter.

SUMMARY OF THE INVENTION

Accordingly, one object of this invention is to provide a novel compound for using with superoxide dismutase to reinforce its anti-free radical action.

The present inventors have now found that this and other objects are achieved using a cosmetic and/or dermatological composition which comprises at least one superoxide dismutase and at least one porphyrin.

Yet another object of the present invention is a method comprising applying to the skin, hair and/or mucosae a composition as described above containing at least one superoxide dismutase and at least one porphyrin.

DESCRIPTION OF THE PREFERRED EMBODIMENTS

Suitable superoxide dismutases in accordance with the present invention are SOD enzymes and any equivalent product which has an activity analogous to that of superoxide dismutases, namely any natural enzyme which is able to catalyze the dismutation reaction indicated above, as well as any product which has this activity, which includes in particular modified enzymes, such as SODs modified by grafting polyoxyalkylenes, polyethylene glycols, polysaccharides or acylated groups, and also substances containing such products.

SOD enzymes which are metalloproteins in which the metallic constituent, for example, iron, manganese, copper and/or zinc, may be of various origins. Particular mention may be made of the SODs of animal origin (for example bovine or porcine), of human origin (for example from placenta or blood), of vegetable origin (for example extracted from fungi, algae, spinach, etc.), or SODs extracted from microorganisms (bacteria or yeasts), or else recombinant SODs obtained by genetic manipulation.

Among the examples of SOD of bovine origin, particular mention may be made of the SOD of Cu—Zn type which has been purified to homogeneity and approved for clinical applications (New Trends in Allergy, I. Ring et al., Ed. Springer Verlag 1986).

Among the SODs obtained from cultures of bacteria, yeasts or animal cells, mention may be made of the recombinant human SOD Cu—Zn marketed by the company UBE Industries Limited.

Among the examples of SODs extracted from bacteria, particular mention may be made of those extracted from *Escherichia coli*; the superoxide dismutases extracted from fungi include in particular those extracted from *Pleurotus*

*olearius*; the superoxide dismutases extracted from blood include erythrocupreins.

It is also possible to mention the superoxide dismutases extracted from marine bacterial strains such as, for example, from the strains *Photobacterium phosphoreum, Photobacterium leiognathi* or *Photobacterium sepia*. Among the various strains which may be used preferred strains include *Photobacterium phosphoreum* No. ATCC 11040, *Photobacterium leiognathi* No. ATCC 25521, *Photobacterium sepia* No. ATCC 15709, *Escherichia coli* No. ATCC 15224 and *Pleurotus olearius* strain Gillet (Laboratoire de Cryptogamie de Paris Parisienne Laboratory of Cryptogamy).

The SODs according to the invention may be prepared by application of methods which have already been described, for example in the article by Keele et al. cited above, and in Eur. J. Rheumatol. and Inflammation, 4, 173–182 (1982).

SODs extracted from marine bacterial strains can be prepared in accordance with the process described in U.S. Pat. No. 3,920,521.

The SODs which are used according to the invention may also be SODs which are modified, in particular, in accordance with the teaching of H. Morimoto, "International Conference on Medical, Biochemical and Chemical Aspects of Free Radicals" (1988 Kyoto) p. 317, or in accordance with Ando Yukio, p. 318 (same source), or else in accordance with JP-A-01250304 (Kanebo) and JP-A-02273176. The modified SODs described in U.S. Pat. No. 5,169,630 and European Patent Application EP-A-426 488 may also be mentioned.

The SODs in accordance with the invention may additionally be used in a form stabilized according to known techniques, for example with the aid of phosphate, in the presence of an alkali metal chloride and sucrose; see, for example, U.S. Pat. No. 4,966,774.

The porphyrins which can be used according to the invention are, in particular, charge transfer porphyrins comprising a bivalent metal chosen from iron, magnesium, copper, zinc and manganese. By way of example, the porphyrins are chosen from chlorophyll, especially chlorophyll a, chlorophyllin, haemoglobin, and plant and/or animal extracts containing chlorophyll or haemoglobin.

A chlorophyll which may be mentioned is chlorophyll a sold by Sigma (St. Louis, Mo.).

Plant extracts which contain chlorophyll and which may be mentioned by way of example are tea extract sold under the name "SUNPHENON" by Nikkol, extract of rosemary sold under the name "ROSMANOX POWDER" by Marcus, aromatized extract of meadow-sweet sold under the name "SUPEXTRAT DE REINE DES PROS" by Sochibo, extract of thyme sold by Sarpap, balm extract sold by the company Sarpap and spinach extract sold under the name "SPINACH ACETONE POWDER" by Sigma.

As haemoglobin, the bovine haemoglobin sold by Sigma may be mentioned.

As chlorophyllin, that sold by Wackherr may be mentioned.

The composition in accordance with the invention finds its principal application in the production of cosmetic and/or dermatological compositions which are intended for preventing and/or combating skin ageing and/or for protecting the skin, hair and/or mucosae against the harmful and/or unaesthetic effects caused by the free radicals induced, in particular, by atmospheric pollutants and/or by ultraviolet radiation. The invention therefore also relates to such compositions.

In the compositions of the invention, the concentration of the SOD may be chosen, for example, in the range from 40 to 5000 enzymatic units of SOD per 100 g of composition, and in particular from 250 to 1500 units. The enzymatic unit of SOD is defined by McCord and Fridovitch, J. Biol. Chem. 244, 6049 (1969).

The amount of porphyrin in the composition is generally in a proportion of from 0.001% to 1% by weight, and in particular from 0.025 % to 0.1% by weight, relative to the total weight of the composition.

The compositions according to the invention may contain SOD and porphyrin either as chief active ingredients or by way of protection against the oxidation of the other ingredients. In the case where the oxidizable ingredients to be protected undergo accelerated decomposition in the presence of keratinous fibers and/or of the skin and/or of the mucosae, the association of SOD and porphyrin may be stored on its own, in dilute or concentrated aqueous solution, or in the form of a complex or a freeze-dried material, and may be added to the other ingredients of the composition only at the time of use.

Similarly, when the association of SOD and porphyrin is used with the aim of maintaining or enhancing the qualities of the skin and/or of the hair and/or of mucosae, this association may be added to the composition only at the time of use.

The compositions according to the invention may therefore be packaged as a number of parts, with a first part containing the SOD and the porphyrin and a second part containing the other ingredients of the composition.

In addition to the binary association of SOD and porphyrin, the compositions for the skin according to the invention may contain active ingredients or excipients which are usually employed in cosmetic or dermatological formulations, such as surfactants, dyes, fragrances, preservatives, emulsifiers, liquid vehicles such as water, fatty substances which are intended to form the fatty phase of emulsions (such as milks or creams), resins, etc.

Suitable compounds useful for forming a fatty phase are, for example, mineral, animal, vegetable or synthetic oils, silicone and/or fluorinated oils, waxes, fatty alcohols or else fatty acids.

Suitable mineral oils include, for example, liquid petroleum, the synthetic oils include ethyl palmitate and isopropyl palmitate, alkyl myristates such as isopropyl, butyl or cetyl myristate, hexyl stearate, triglycerides of octanoic and decanoic acids (for example the products sold under the name "MIGLYOL" by Dynamit-Nobel), cetyl ricinoleate, stearyl octanoate (purcellin oil) and hydroxylated polyisobutene octanoate.

Suitable vegetable oils include, for example, sweet almond oil, avocado oil, coconut oil, wheatgerm oil, corn oil, castor oil, olive oil, palm oil, sesame oil, soya oil, argan oil, evening primrose oil, borage oil, essential oils and vegetable waxes such as beeswax.

Suitable fatty alcohols include cetyl alcohol, stearyl alcohol, myristyl alcohol, hydroxystearyl alcohol, oleyl alcohol, isostearyl alcohol, lauryl alcohol, hexadecyl alcohol, ricinoleyl alcohol, behenyl alcohol, erucyl alcohol and 2-octyldodecanol.

Suitable fatty acids include stearic acid, myristic acid, palmitic acid, oleic acid, linoleic acid, lauric acid, isostearic acid, hydroxystearic acid, linolenic acid, ricinoleic acid, arachidic acid, behenic acid, erucic acid and lanolinic acids.

The compositions according to the invention which are intended for topical application are, in particular, solutions or dispersions of the lotion or serum type, emulsions of liquid or semiliquid consistency of the milk type, which are obtained by dispersing a fatty phase in an aqueous phase (O/W) or vice versa (W/O), or suspensions or emulsions of soft consistency, of the cream or gel type, or else microgranules, or vesicular dispersions of ionic and/or nonionic type.

These compositions are prepared by the usual methods. They constitute, in particular, cleansing creams, protection creams or beauty creams for the face, hands or body (for example day creams, night creams, make-up removal creams, foundation creams, anti-sun creams), liquid foundations, make-up removal milks, body-protecting or body care milks, anti-sun milks, skin care lotions, gels or mousses such as cleansing lotions, anti-sun lotions, artificial tanning lotions, compositions for the bath or deodorizing compositions containing a bactericidal agent.

The compositions according to the invention may also consist of solid preparations which constitute soaps or cleansing cakes.

The compositions may also be packaged in the form of an aerosol composition also containing a pressurized propellant.

The compositions for hair according to the invention may be presented in the form of aqueous, alcoholic or aqueous-alcoholic solutions or in the form of creams, gels, emulsions or mousses or else in the form of an aerosol composition also containing a pressurized propellant.

Besides the conventional active ingredients, they may include various adjuvants which are usually present in these compositions for hair, for example liquid or gel-form vehicles, fragrances, dyes, preservatives, thickeners, etc.

The quantities of the various constituents of the compositions according to the invention are those which are conventionally employed in fields in question.

The association according to the invention may be incorporated as the chief ingredient or as a secondary ingredient in various compositions for hair care which constitute, for example, creams, lotions, gels, serums or mousses for the care of the scalp, shampoos, hair-setting lotions, treating lotions, styling creams or gels, dye compositions (especially oxidation dyes) optionally in the form of dyeing shampoos, restructuring lotions for hair, permanent wave compositions (especially compositions for the first step of a permanent waving operation), lotions or gels to combat hair loss, etc.

The compositions of the invention may in particular be shampoos containing, in addition to a superoxide dismutase and a porphyrin, a cationic, anionic or nonionic detergent; dyeing compositions, including coloring shampoos, which contain dyes or usual dye precursors; compositions for the first step (reduction step) of a hair-reshaping operation, containing reducing derivatives such as mercaptans, sulphites, etc; compositions for slowing down the loss of hair and for promoting the regrowth of hair, containing compounds such as minoxidil (2,4-diamino-6-piperidinopyrimidine 3-oxide) and derivatives thereof, diazoxide (7-chloro-3-methyl-1,2,4-benzothiadiazine 1,1-dioxide) and phenytoin (5,5-diphenylimidazolidine-2,4-dione).

The cosmetic compositions of the invention may also be for oral and dental use, for example a toothpaste. In this case the compositions may contain usual adjuvants and additives for compositions for oral use, and in particular surfactants, thickeners, moisturizers, polishing agents such as silica, various active ingredients such as fluorides, in particular sodium fluoride, and optionally sweetening agents such as sodium saccharinate.

The cosmetic compositions according to the invention may be either compositions which are ready for use, or concentrates which must be diluted before use. The compositions which can be presented in the form of concentrates are, for example, shampoos or compositions for baths.

The method of cosmetic treatment of the invention may be employed, in particular, by applying the hygienic or cosmetic compositions as defined above in accordance with the utilization technique which is conventional for these compositions, for example: application of creams, of gels, of serums, of lotions, of make-up removal milks or anti-sun compositions to the skin or hair, application of a hair lotion to wet hair, shampooing, or else application of a dentifrice to the gums.

The method of cosmetic treatment of the invention is employed so as to apply an effective quantity of the association of SOD and porphyrin, that is to say a quantity which is sufficient to obtain the desired protective effect.

This method of cosmetic treatment is intended in particular to maintain the keratinous structure of the skin or hair, so as to avoid the degradation of the latter and the unaesthetic effects of such a degradation under the influence of the free radicals which are induced, in particular, by atmospheric pollutants, to maintain or enhance the qualities of the skin (softness, suppleness, elasticity), of the hair or of the mucosae, to protect the skin or hair against the harmful effects of ultraviolet rays, and in particular to treat or prevent premature ageing of the skin.

Having generally described this invention, a further understanding can be obtained by reference to certain specific examples which are provided herein for purposes of illustration only and are not intended to be limiting unless otherwise specified.

EXAMPLES

In the following examples the proportions indicated are percentages by weight.
Formulation examples:

Example 1

Oil-in-water emulsion

| | |
|---|---|
| SOD (sold by Pentapharm and assaying at 3.13 U/mg), qs 600 units | 0.20 |
| Green tea extract ("SUNPHENON" from Nikkol) | 0.05 |
| Polyethylene glycol polyoxyethylenated with 50 moles of ethylene oxide | 1.50 |
| Diglyceryl monostearate | 1.50 |
| Liquid paraffin | 24.00 |
| Cetyl alcohol | 2.50 |
| Triethanolamine | qs pH 7 |
| Water | qs 100 |

This emulsion, prepared in a usual manner, may be employed in particular as a day cream.

Example 2

Water-in-oil emulsion

| | |
|---|---|
| SOD (sold by Bio-technologie and assaying at 8037 U/mg), qs 1000 units | 0.00012 |
| Chlorophyllin (sold by Wackherr) | 0.1 |
| Polyglyceryl sesquiisostearate | 4.0 |

-continued

| | |
|---|---|
| White beeswax | 0.5 |
| Magnesium stearate | 1.5 |
| Aluminum stearate | 1.0 |
| Hydrogenated castor oil, polyoxyethylenated (with 7 moles of ethylene oxide) | 3.0 |
| Isopropyl palmitate | 10.0 |
| Perhydrosqualene | 15.0 |
| Water | qs to 100% |

This emulsion, prepared in a usual manner, can be used in particular as a beauty cream.

Example 3

Vesicular dispersion

| | |
|---|---|
| Nonionic amphiphile* | 0.9 |
| Sodium acylglutamate HS21 (sold by Ajinomoto) | 0.1 |
| Glycerine | 3.0 |
| SOD (as in Example 1) qs 250 units | 0.08 |
| Spinach extract (sold by Sigma) | 0.1 |
| Perhydrosqualene | 10.0 |
| Methyl para-hydroxybenzoate | 0.2 |
| Crosslinked polyacrylic acid ("CARBOPOL 940" sold by Goodrich) | 0.4 |
| Triethanolamine | qs pH = 7 |
| Water | qs 100% |

*The nonionic amphiphile is a mixture of products corresponding to the following formula:

$$C_{12}H_{25}[OC_2H_3(R)-O-C_3H_5(OH)-O]_n-H$$

in which:

n, denoting the average number of units, is equal to 2.7, the groups $-OC_2H_3(R)-$ denote radicals:

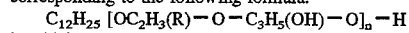

and the groups $-C_3H_5(OH)-O-$ denote radicals:

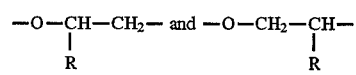

where R denotes the radicals $C_{14}H_{29}$ and $C_{16}H_{33}$, statistically in equal molar quantities.

The product sold under the name "ACYLGLUTAMATE HS21", is a disodium stearyl glutamate.

This vesicular dispersion was prepared as follows:

the nonionic amphiphilic compound was added to the cholesterol and to the acylglutamate at a temperature of 100° C.;

the temperature was lowered to 90° C. and the glycerin, spinach extract and water were added at this temperature;

the mixture was cooled to 50° C., the SOD was added, and then the mixture was homogenized for twice four minutes with the aid of a Virtis 60 homogenizer (at 40,000 revolutions per minute);

the product obtained was cooled rapidly to ambient temperature and diluted with 20 g of water. The oily phase (perhydrosqualene and methyl parahydroxybenzoate) was added and then the mixture was homogenized for twice four minutes at 40,000 revolutions per minute;

the Carbopol gel ("CARBOPOL 940" and water qs 100 g) was dispersed for 30 seconds at 10,000 revolutions per minute and the whole was then neutralized with triethanolamine.

A smooth and shiny cream was obtained which can be used, in particular, as a beauty cream.

Test for inhibition of the production of ethylene:

The following were introduced into a Petri dish 32 mm in diameter in the following order:

1.4 ml of 50 mM phosphate buffer (pH=7.4),

100 μl of 200 mM methionine solution,

100 μl of 4 mM ferric chloride solution,

100 μl of the product to be tested,

100 μl of 4 mM EDTA (ethylenediaminetetraacetic acid) solution,

100 μl of 400 mM NADH (nicotinamide adenine dinucleotide, reduced form) solution, 100 μl of 2 mM riboflavin solution.

The sample had a total volume of 2 ml.

This dish was then placed on a small aluminum cup and covered with a quartz cell in order to be exposed to UVA (365 nm) at a dose of 1 J/cm². The composition comprising NADH, riboflavin, ferric chloride and EDTA, when subjected to UVA exposure, will generate reduced oxygen species: $O_2^-$, $H_2O_2$, and chiefly the hydroxyl radical OH. The latter will react with methionine, liberating ethylene, the quantity of which is measured by gas chromatography.

The greater the quantity of free radicals formed, the greater the quantity of ethylene given off. The results were expressed as a percentage of inhibitory power, corresponding to the percentage reduction in the production of ethylene relative to the control (containing 100 μl of phosphate buffer in place of the product to be tested).

The substances studied were introduced using a micropipette. They were:

the SOD (source: Sigma, assaying at 400 units per mg), chlorophyll a (source: Sigma), chlorophyllin (source: Wackherr) and bovine haemoglobin (source: Sigma).

Chromatography conditions: (Varian 3740 instrument)

injector temperature: 80° C., column temperature: 80° C., detector temperature: 250° C.

helium pressure: 36 psi (corresponding to approximately $2.4 \times 10^5$ Pa), column: 60/80 mesh F1 alumina (source: Supelco), length: 2 m, external diameter: ⅛.

The results (mean of 3 tests) are collated in the following table:

| Sample | Sigma SOD (units/ ml of sample) | Chlorophyll a % g/ 100 ml | Chlorophyllin % g/ 100 ml | Haemoglobin % g/ 100 ml | % Inhibitory power | Increase in Inhibitory power |
|---|---|---|---|---|---|---|
| E₁ | 1 | — | — | — | 33.8 | — |
| E₂ | — | 0.015 | — | — | 21.4 | — |
| E₃ | 0.5 | 0.0075 | — | — | 60.1 | 78% |
| E₄ | 50 | — | — | — | 55.8 | — |
| E₅ | — | — | 0.005 | — | 31.7 | — |
| E₆ | 25 | — | 0.0025 | — | 63.5 | 14% |
| E₇ | 50 | — | — | — | 55.8 | — |
| E₈ | — | — | — | 0.025 | 42.1 | — |
| E₉ | — | — | — | 0.05 | 68.8 | — |
| E₁₀ | — | — | — | 0.075 | 76.3 | — |
| E₁₁ | 25 | — | — | 0.0125 | 76.1 | 28% |
| E₁₂ | 25 | — | — | 0.025 | 80.1 | 16.4% |
| E₁₃ | 25 | — | — | 0.0375 | 84.0 | 10.1% |
| E₁₄ | 15 | — | — | — | 46.5 | — |
| E₁₅ | — | — | — | 0.025 | 42.1 | — |
| E₁₆ | 7.5 | — | — | 0.0125 | 61.9 | 33.1% |

The percentages indicated are by weight. One unit of SOD corresponds to 2.5 μg.

In order to calculate the increase in inhibitory power of the association, the percentage increase in inhibitory power of the association relative to the inhibitory power of the compound of the association which, on its own, gives the highest percentage of inhibitory power, was determined.

The study of these results by 1-factor variance analysis shows that they are statistically significant.

The sample $E^3$ shows that, by combining SOD and chlorophyll a, an inhibitory power is obtained which is much greater than that of the lone SOD of sample $E_1$, used in a quantity which is double that used in association, or than that of the lone chlorophyll a of the sample $E_2$, used in a quantity which is double that used in the association.

Likewise, the sample $E_6$ shows that, by combining SOD and chlorophyllin, an inhibitory power is obtained which is significantly greater than that of the lone SOD of the sample $E_4$, used in a quantity double that used in the association, or than that of the lone chlorophyllin of the sample $E_5$, used in a quantity double that used in the association.

The same applies to samples $E_{11}$, to $E_{13}$ and $E_{16}$, which show that the association of SOD and haemoglobin gives an inhibitory power which is significantly greater than that of the lone SOD of samples $E_7$ and $E_{14}$, used in a quantity double that used in the association, or than that of the lone haemoglobin of samples $E_8$ to $E_{10}$ and $E_{15}$, used in a quantity double that used in the association.

Having now fully described the invention, it will be apparent to one of ordinary skill in the art that many changes and modifications can be made thereto without departing from the spirit or scope of the invention as set forth herein.

What is claimed and new and desired to be secured by Letters Patent of the United States is:

1. A composition comprising synergistically effective amounts of at least one superoxide dismutase (SOD) and at least one porphyrin selected from the group consisting of chlorophyll a, chlorophyllin and haemoglobin.

2. The composition of claim 1, wherein said superoxide dismutase is an enzyme capable of catalyzing the dismutation reaction of superoxide ions.

3. The composition of claim 1, wherein said porphyrin is a charge transfer porphyrin.

4. The composition of claim 1, wherein said porphyrin is a vegetable or animal extract containing chlorophyll a, chlorophyllin, haemoglobin or a mixture thereof.

5. The composition of claim 1, wherein the concentration of said superoxide dismutase is within the range from 40 to 5000 enzymatic units per 100 g of composition.

6. The composition of claim 5, wherein said concentration of the superoxide dismutase is within the range from 250 to 1500 enzymatic units per 100 g of composition.

7. The composition of claim 1, wherein said porphyrin is present in a proportion of from 0.001% to 1% by weight, relative to the total weight of the composition.

8. The composition of claim 7, wherein said porphyrin is present in a proportion of from 0.025% to 0.1% by weight, relative to the total weight of the composition.

9. The composition of claim 1, comprising at least one superoxide dismutase and chlorophyll a.

10. The composition of claim 1, comprising at least one superoxide dismutase and chlorophyllin.

11. The composition of claim 1, comprising at least one superoxide dismutase and haemoglobin.

* * * * *